(12) United States Patent
Jackson

(10) Patent No.: US 8,540,753 B2
(45) Date of Patent: Sep. 24, 2013

(54) POLYAXIAL BONE SCREW WITH UPLOADED THREADED SHANK AND METHOD OF ASSEMBLY AND USE

(76) Inventor: Roger P. Jackson, Prairie Village, KS (US)

( * ) Notice: Subject to any disclaimer, the term of this patent is extended or adjusted under 35 U.S.C. 154(b) by 1309 days.

(21) Appl. No.: 10/958,743

(22) Filed: Oct. 5, 2004

(65) Prior Publication Data
US 2006/0084979 A1    Apr. 20, 2006

Related U.S. Application Data

(63) Continuation-in-part of application No. 10/409,935, filed on Apr. 9, 2003, now Pat. No. 6,964,666.

(51) Int. Cl.
*A61B 17/70*    (2006.01)
(52) U.S. Cl.
USPC .......................................................... 606/266
(58) Field of Classification Search
USPC .................... 411/340; 606/61, 300–331
See application file for complete search history.

(56) References Cited

U.S. PATENT DOCUMENTS

| | | | | |
|---|---|---|---|---|
| 2,362,999 A | * | 11/1944 | Hewitt | 411/403 |
| 2,531,892 A | * | 11/1950 | Reese | 403/11 |
| 2,813,450 A | * | 11/1957 | Dzus | 411/403 |
| 3,013,244 A | * | 12/1961 | Rudy | 439/777 |
| 4,033,139 A | * | 7/1977 | Frederick | 405/228 |
| 4,448,191 A | | 5/1984 | Rodnyansky et al. | |
| 4,743,260 A | | 5/1988 | Burton | |
| 4,748,260 A | | 5/1988 | Marlett | |
| 4,759,672 A | * | 7/1988 | Nilsen et al. | 411/375 |
| 4,836,196 A | | 6/1989 | Park et al. | |
| 4,946,458 A | | 8/1990 | Harms et al. | |
| 5,019,080 A | * | 5/1991 | Hemer | 606/73 |
| 5,129,388 A | | 7/1992 | Vignaud et al. | |
| 5,176,678 A | | 1/1993 | Tsou | |
| 5,176,680 A | | 1/1993 | Vignaud et al. | |
| 5,180,393 A | | 1/1993 | Commarmond | |
| 5,207,678 A | | 5/1993 | Harms et al. | |
| 5,261,912 A | | 11/1993 | Frigg | |
| 5,282,863 A | | 2/1994 | Burton | |
| 5,312,404 A | | 5/1994 | Asher et al. | |
| 5,360,431 A | | 11/1994 | Puno et al. | |
| 5,375,823 A | | 12/1994 | Navas | |
| 5,395,371 A | | 3/1995 | Miller et al. | |
| 5,415,661 A | | 5/1995 | Holmes | |

(Continued)

FOREIGN PATENT DOCUMENTS

DE    9202745    4/1992
DE    19507141    9/1996

(Continued)

OTHER PUBLICATIONS

*EBI Omega 21 Brochure*, EBI Spine Systems, pub. 1999.

(Continued)

*Primary Examiner* — Mary Hoffman
(74) *Attorney, Agent, or Firm* — John C. McMahon

(57) ABSTRACT

A polyaxial bone screw assembly includes a threaded shank body integral with an upper capture structure and a head having an inner cavity for receiving the capture structure. The capture structure is threaded and the head includes a threaded opening for rotatable assembly with the capture structure and eventual locking frictional engagement between the capture structure and the head.

27 Claims, 6 Drawing Sheets

(56) References Cited

U.S. PATENT DOCUMENTS

| | | | |
|---|---|---|---|
| 5,423,816 | A | 6/1995 | Lin |
| 5,429,639 | A | 7/1995 | Judet |
| 5,443,467 | A | 8/1995 | Biedermann et al. |
| 5,466,237 | A * | 11/1995 | Byrd et al. .................. 606/61 |
| 5,474,555 | A | 12/1995 | Puno et al. |
| 5,476,462 | A | 12/1995 | Allard et al. |
| 5,476,464 | A | 12/1995 | Metz-Stavenhagen et al. |
| 5,480,401 | A | 1/1996 | Navas |
| 5,489,307 | A | 2/1996 | Kuslich et al. |
| 5,496,321 | A | 3/1996 | Puno et al. |
| 5,540,688 | A | 7/1996 | Navas |
| 5,554,157 | A | 9/1996 | Errico et al. |
| 5,569,247 | A | 10/1996 | Morrison |
| 5,584,834 | A | 12/1996 | Errico et al. |
| 5,586,984 | A | 12/1996 | Errico et al. |
| 5,591,166 | A | 1/1997 | Bernhardt et al. |
| 5,601,553 | A | 2/1997 | Trebing et al. |
| 5,607,426 | A | 3/1997 | Ralph et al. |
| 5,647,873 | A | 7/1997 | Errico et al. |
| 5,669,911 | A | 9/1997 | Errico et al. |
| 5,672,175 | A | 9/1997 | Martin |
| 5,672,176 | A | 9/1997 | Biedermann et al. |
| 5,681,319 | A | 10/1997 | Biedermann et al. |
| 5,690,630 | A | 11/1997 | Errico et al. |
| 5,716,356 | A | 2/1998 | Biedermann et al. |
| 5,725,528 | A * | 3/1998 | Errico et al. .................. 606/61 |
| 5,728,098 | A | 3/1998 | Sherman et al. |
| 5,733,286 | A | 3/1998 | Errico et al. |
| 5,738,685 | A | 4/1998 | Halm et al. |
| 5,782,833 | A | 7/1998 | Haider |
| 5,797,911 | A | 8/1998 | Sherman et al. |
| 5,800,435 | A | 9/1998 | Errico et al. |
| 5,817,094 | A | 10/1998 | Errico et al. |
| 5,863,293 | A | 1/1999 | Richelsoph |
| 5,876,402 | A | 3/1999 | Errico et al. |
| 5,879,350 | A | 3/1999 | Sherman et al. |
| 5,879,351 | A | 3/1999 | Viart |
| 5,882,350 | A | 3/1999 | Ralph et al. |
| 5,885,286 | A | 3/1999 | Sherman et al. |
| 5,891,145 | A | 4/1999 | Morrison et al. |
| 5,902,303 | A | 5/1999 | Eckhof et al. |
| RE36,221 | E | 6/1999 | Breard et al. |
| 5,954,725 | A | 9/1999 | Sherman et al. |
| 5,961,517 | A | 10/1999 | Biedermann et al. |
| 5,964,760 | A | 10/1999 | Richelsoph |
| 6,010,503 | A | 1/2000 | Richelsoph et al. |
| 6,019,759 | A | 2/2000 | Rogozinski |
| 6,022,350 | A | 2/2000 | Ganem |
| 6,053,917 | A | 4/2000 | Sherman et al. |
| 6,063,090 | A | 5/2000 | Schlapfer |
| 6,074,391 | A | 6/2000 | Metz-Stavenhagen et al. |
| 6,077,262 | A | 6/2000 | Schlapfer et al. |
| 6,086,588 | A | 7/2000 | Ameil et al. |
| 6,090,110 | A | 7/2000 | Metz-Stavenhagen |
| 6,090,111 | A | 7/2000 | Nichols |
| 6,099,528 | A | 8/2000 | Saurat |
| 6,110,172 | A | 8/2000 | Jackson |
| 6,113,601 | A | 9/2000 | Tatar |
| 6,132,431 | A | 10/2000 | Nilsson et al. |
| 6,132,432 | A | 10/2000 | Richelsoph |
| 6,132,434 | A | 10/2000 | Sherman et al. |
| 6,136,002 | A | 10/2000 | Shih et al. |
| 6,146,383 | A | 11/2000 | Studer et al. |
| 6,183,472 | B1 | 2/2001 | Lutz |
| 6,186,718 | B1 * | 2/2001 | Fogard .................. 411/403 |
| 6,187,005 | B1 | 2/2001 | Brace et al. |
| 6,214,012 | B1 * | 4/2001 | Karpman et al. .................. 606/93 |
| RE37,161 | E | 5/2001 | Michelson et al. |
| 6,224,596 | B1 | 5/2001 | Jackson |
| 6,241,730 | B1 | 6/2001 | Alby |
| 6,248,105 | B1 | 6/2001 | Schlapfer et al. |
| 6,254,602 | B1 | 7/2001 | Justis |
| 6,267,764 | B1 | 7/2001 | Elberg |
| 6,267,765 | B1 | 7/2001 | Taylor |
| 6,273,888 | B1 | 8/2001 | Justis |
| 6,280,442 | B1 | 8/2001 | Barker et al. |
| 6,280,445 | B1 | 8/2001 | Morrison et al. |
| 6,287,308 | B1 | 9/2001 | Betz et al. |
| 6,287,311 | B1 | 9/2001 | Sherman et al. |
| 6,296,643 | B1 | 10/2001 | Hopf et al. |
| 6,299,613 | B1 | 10/2001 | Ogilvie et al. |
| 6,302,888 | B1 | 10/2001 | Mellinger et al. |
| 6,309,391 | B1 | 10/2001 | Crandall |
| 6,331,179 | B1 | 12/2001 | Freid et al. |
| 6,355,040 | B1 | 3/2002 | Richelsoph et al. |
| RE37,665 | E | 4/2002 | Ralph et al. |
| 6,368,321 | B1 * | 4/2002 | Jackson .................. 606/61 |
| 6,402,752 | B2 | 6/2002 | Schaffler-Wachter |
| 6,440,137 | B1 | 8/2002 | Horvath et al. |
| 6,451,021 | B1 | 9/2002 | Ralph |
| 6,471,703 | B1 | 10/2002 | Ashman |
| 6,471,705 | B1 | 10/2002 | Biedermann et al. |
| 6,485,491 | B1 | 11/2002 | Farris |
| 6,485,494 | B1 | 11/2002 | Haider |
| 6,488,681 | B2 | 12/2002 | Martin et al. |
| 6,508,818 | B2 | 1/2003 | Steiner et al. |
| 6,520,962 | B1 | 2/2003 | Taylor et al. |
| 6,527,804 | B1 | 3/2003 | Gauchet et al. |
| 6,530,929 | B1 | 3/2003 | Justis et al. |
| 6,533,786 | B1 | 3/2003 | Needham et al. |
| 6,547,790 | B2 | 4/2003 | Harkey, III et al. |
| 6,551,320 | B2 | 4/2003 | Liebermann |
| 6,554,831 | B1 | 4/2003 | Rivard et al. |
| 6,554,832 | B2 | 4/2003 | Shluzas |
| 6,554,834 | B1 | 4/2003 | Crozet et al. |
| 6,558,387 | B2 | 5/2003 | Errico et al. |
| 6,562,040 | B1 | 5/2003 | Wagner |
| 6,565,565 | B1 | 5/2003 | Yuan et al. |
| 6,565,567 | B1 | 5/2003 | Haider |
| 6,582,436 | B2 | 6/2003 | Schlapfer et al. |
| 6,582,466 | B1 | 6/2003 | Gauchet |
| 6,585,740 | B2 | 7/2003 | Schlapfer et al. |
| 6,595,992 | B1 | 7/2003 | Wagner et al. |
| 6,595,993 | B2 | 7/2003 | Donno et al. |
| 6,610,063 | B2 | 8/2003 | Kumar et al. |
| 6,613,050 | B1 | 9/2003 | Wagner et al. |
| 6,623,485 | B2 | 9/2003 | Doubler et al. |
| 6,626,907 | B2 | 9/2003 | Campbell et al. |
| 6,626,908 | B2 | 9/2003 | Cooper et al. |
| 6,635,059 | B2 | 10/2003 | Randall et al. |
| 6,648,885 | B1 | 11/2003 | Friesem |
| 6,648,887 | B2 | 11/2003 | Ashman |
| 6,652,765 | B1 | 11/2003 | Beaty |
| 6,656,179 | B1 | 12/2003 | Schaefer et al. |
| 6,656,181 | B2 | 12/2003 | Dixon et al. |
| 6,660,004 | B2 | 12/2003 | Barker et al. |
| 6,663,632 | B1 | 12/2003 | Frigg |
| 6,663,635 | B2 | 12/2003 | Frigg et al. |
| 6,673,073 | B1 | 1/2004 | Schafer |
| 6,676,661 | B1 | 1/2004 | Benlloch |
| 6,679,833 | B2 | 1/2004 | Smith et al. |
| 6,682,529 | B2 | 1/2004 | Stahurski |
| 6,682,530 | B2 | 1/2004 | Dixon et al. |
| 6,689,133 | B2 | 2/2004 | Morrison et al. |
| 6,689,134 | B2 | 2/2004 | Ralph et al. |
| 6,695,843 | B2 | 2/2004 | Biedermann et al. |
| 6,695,851 | B2 | 2/2004 | Zdeblick et al. |
| 6,699,249 | B2 | 3/2004 | Schlapfer et al. |
| 6,706,045 | B2 | 3/2004 | Lin et al. |
| 6,712,818 | B1 | 3/2004 | Michelson |
| 6,716,213 | B2 | 4/2004 | Shitoto |
| 6,716,214 | B1 | 4/2004 | Jackson |
| 6,716,247 | B2 | 4/2004 | Michelson |
| 6,723,100 | B2 | 4/2004 | Biederman |
| 6,730,093 | B2 | 5/2004 | Saint Martin |
| 6,730,127 | B2 | 5/2004 | Michelson |
| 6,733,502 | B2 | 5/2004 | Altarac et al. |
| 6,736,816 | B2 | 5/2004 | Ritland |
| 6,736,820 | B2 | 5/2004 | Biedermann et al. |
| 6,740,086 | B2 | 5/2004 | Richelsoph |
| 6,746,449 | B2 | 6/2004 | Jones et al. |
| 6,755,829 | B1 | 6/2004 | Bono |
| 6,755,835 | B2 | 6/2004 | Schultheiss et al. |
| 6,755,836 | B1 | 6/2004 | Lewis |

| | | |
|---|---|---|
| 6,761,723 B2 | 7/2004 | Butterman et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,066,062 B2 * | 6/2006 | Flesher .................. 81/442 |
| 2001/0001119 A1 | 5/2001 | Lombardo |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0035366 A1 | 3/2002 | Walder et al. |
| 2002/0045898 A1 | 4/2002 | Freid et al. |
| 2002/0058942 A1 | 5/2002 | Biedermann |
| 2002/0082602 A1 | 6/2002 | Biedermann et al. |
| 2002/0111626 A1 | 8/2002 | Ralph et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 * | 1/2003 | Biedermann et al. .......... 606/73 |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann |
| 2003/0149432 A1 | 8/2003 | Frigg et al. |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2003/0220642 A1 | 11/2003 | Freudiger |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 * | 5/2004 | Lourdel et al. ................. 606/61 |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Jahng |
| 2005/0070899 A1 | 3/2005 | Doubler et al. |
| 2005/0080415 A1 | 4/2005 | Keyer et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0260058 A1 * | 11/2005 | Cassagne, III ................ 411/402 |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |

| | | | | | | |
|---|---|---|---|---|---|---|
| 2005/0267474 | A1 | 12/2005 | Dalton | FR | 2729291 | 7/1996 |
| 2005/0273099 | A1 | 12/2005 | Baccelli et al. | FR | 2796545 | 1/2001 |
| 2005/0273101 | A1 | 12/2005 | Schumacher | FR | 2799949 | 4/2001 |
| 2005/0277919 | A1 | 12/2005 | Slivka et al. | FR | 2856578 | 6/2003 |
| 2005/0277922 | A1 | 12/2005 | Trieu et al. | FR | 2865373 | 1/2004 |
| 2005/0277923 | A1 | 12/2005 | Sweeney | FR | 2865375 | 1/2004 |
| 2005/0277925 | A1 | 12/2005 | Mujwid | FR | 2865377 | 1/2004 |
| 2005/0277927 | A1 | 12/2005 | Guenther et al. | FR | 2857850 | 4/2004 |
| 2005/0277928 | A1 | 12/2005 | Boschert | FR | 2865378 | 10/2004 |
| 2005/0283152 | A1 | 12/2005 | Lindemann et al. | GB | 9202745.8 | 4/1992 |
| 2005/0283157 | A1 | 12/2005 | Coates et al. | GB | 2365345 | 2/2002 |
| 2005/0283238 | A1 | 12/2005 | Reiley | GB | 2382304 | 5/2003 |
| 2005/0283244 | A1 | 12/2005 | Gordon et al. | JP | 2000325358 | 3/2000 |
| 2005/0288669 | A1 | 12/2005 | Abdou | WO | WO01/45576 | 6/2001 |
| 2005/0288670 | A1 | 12/2005 | Panjabi | WO | WO01/49191 | 7/2001 |
| 2005/0288671 | A1 | 12/2005 | Yuan et al. | WO | WO02/054966 | 7/2002 |
| 2005/0288672 | A1 | 12/2005 | Ferree | WO | WO02/102259 | 12/2002 |
| 2005/0288673 | A1 | 12/2005 | Catbagan et al. | WO | WO03/026523 | 4/2003 |
| 2006/0004357 | A1 | 1/2006 | Lee et al. | WO | WO03/068088 | 8/2003 |
| 2006/0004359 | A1 | 1/2006 | Kramer et al. | WO | WO2004/041100 | 5/2004 |
| 2006/0004360 | A1 | 1/2006 | Kramer et al. | WO | WO2004/075778 | 9/2004 |
| 2006/0004363 | A1 | 1/2006 | Brockmeyer et al. | WO | WO2004/089245 | 10/2004 |
| 2006/0009767 | A1 | 1/2006 | Kiester | WO | WO2004/107997 | 12/2004 |
| 2006/0009768 | A1 | 1/2006 | Ritland | WO | WO2005/000136 | 1/2005 |
| 2006/0009769 | A1 | 1/2006 | Liebermann | WO | WO2005/000137 | 1/2005 |
| 2006/0009770 | A1 | 1/2006 | Speirs et al. | WO | WO2005/020829 | 3/2005 |
| 2006/0009846 | A1 | 1/2006 | Trieu et al. | WO | WO2005/065374 | 7/2005 |
| 2006/0015099 | A1 | 1/2006 | Cannon et al. | WO | WO2005/065375 | 7/2005 |
| 2006/0015104 | A1 | 1/2006 | Dalton | WO | WO2005/072632 | 8/2005 |
| 2006/0025767 | A1 | 2/2006 | Khalili | WO | WO2005/082262 | 9/2005 |
| 2006/0025768 | A1 | 2/2006 | Iott et al. | WO | WO2005/099400 | 10/2005 |
| 2006/0025770 | A1 | 2/2006 | Schlapfer et al. | WO | WO2005/104969 | 11/2005 |
| 2006/0036240 | A1 | 2/2006 | Colleran et al. | WO | WO2006/012088 | 2/2006 |
| 2006/0036242 | A1 | 2/2006 | Nilsson et al. | WO | WO2006/017616 | 2/2006 |
| 2006/0036244 | A1 | 2/2006 | Spitler et al. | WO | WO2006/028537 | 3/2006 |
| 2006/0036246 | A1 | 2/2006 | Carl et al. | | | |
| 2006/0036252 | A1 | 2/2006 | Baynham et al. | | | |
| 2006/0036256 | A1 | 2/2006 | Carl et al. | | | |
| 2006/0036259 | A1 | 2/2006 | Carl et al. | | | |
| 2006/0036323 | A1 | 2/2006 | Carl et al. | | | |
| 2006/0036324 | A1 | 2/2006 | Sachs et al. | | | |
| 2006/0041259 | A1 | 2/2006 | Paul et al. | | | |
| 2006/0052780 | A1 | 3/2006 | Errico et al. | | | |
| 2006/0052783 | A1 | 3/2006 | Dant et al. | | | |
| 2006/0052784 | A1 | 3/2006 | Dant et al. | | | |
| 2006/0052786 | A1 | 3/2006 | Dant et al. | | | |
| 2006/0058788 | A1 | 3/2006 | Hammer et al. | | | |
| 2006/0058790 | A1 | 3/2006 | Carl et al. | | | |
| 2006/0064090 | A1 | 3/2006 | Park | | | |
| 2006/0064091 | A1 | 3/2006 | Ludwig et al. | | | |
| 2006/0064092 | A1 | 3/2006 | Howland | | | |

FOREIGN PATENT DOCUMENTS

| | | |
|---|---|---|
| EP | 0667127 | 8/1995 |
| EP | 0677277 | 10/1995 |
| EP | 1121902 | 8/2001 |
| EP | 1190678 | 3/2002 |
| EP | 1570795 | 9/2005 |
| EP | 1579816 | 9/2005 |
| EP | 1634537 | 3/2006 |
| FR | 2717370 | 9/1995 |
| FR | 2718946 | 10/1995 |

OTHER PUBLICATIONS

*Claris Instrumentation* Brochure, G Med, pub. 1997.
*VLS System Variable Locking Screw* Brochure, Interpore Cross International, 1999.
*Contour Spinal System* Brochure, Ortho Development, no publish date.
*Xia Spinal System* Brochure, Stryker Howmedica Osteonics, no publish date.
*The Rod Plate System* Brochure, Stryker Howmedica Osteonics, pub. Oct. 1999.
*Silhouette Spinal Fixation System* Brochure, Sulzer Medica Spine-Tech, no publish date.
*Versalok Low Back Fixation System* Brochure, Wright Medical Technology, Inc., pub. 1997.
*The Strength of Innovation* Advertisement, Blackstone Medical Inc., no publish date.
*The Moss Miami 6.0mm System* Advertisement, author unknown, no publish date.
CD Horizon M8 Multi Axial Screw Spinal System Brochure, Medtronic Sofamor Danek, no publish date.
SDRS Surgical Dynamics Rod System Brochure, Surgical Dynamics, pub. 1998-99.

* cited by examiner

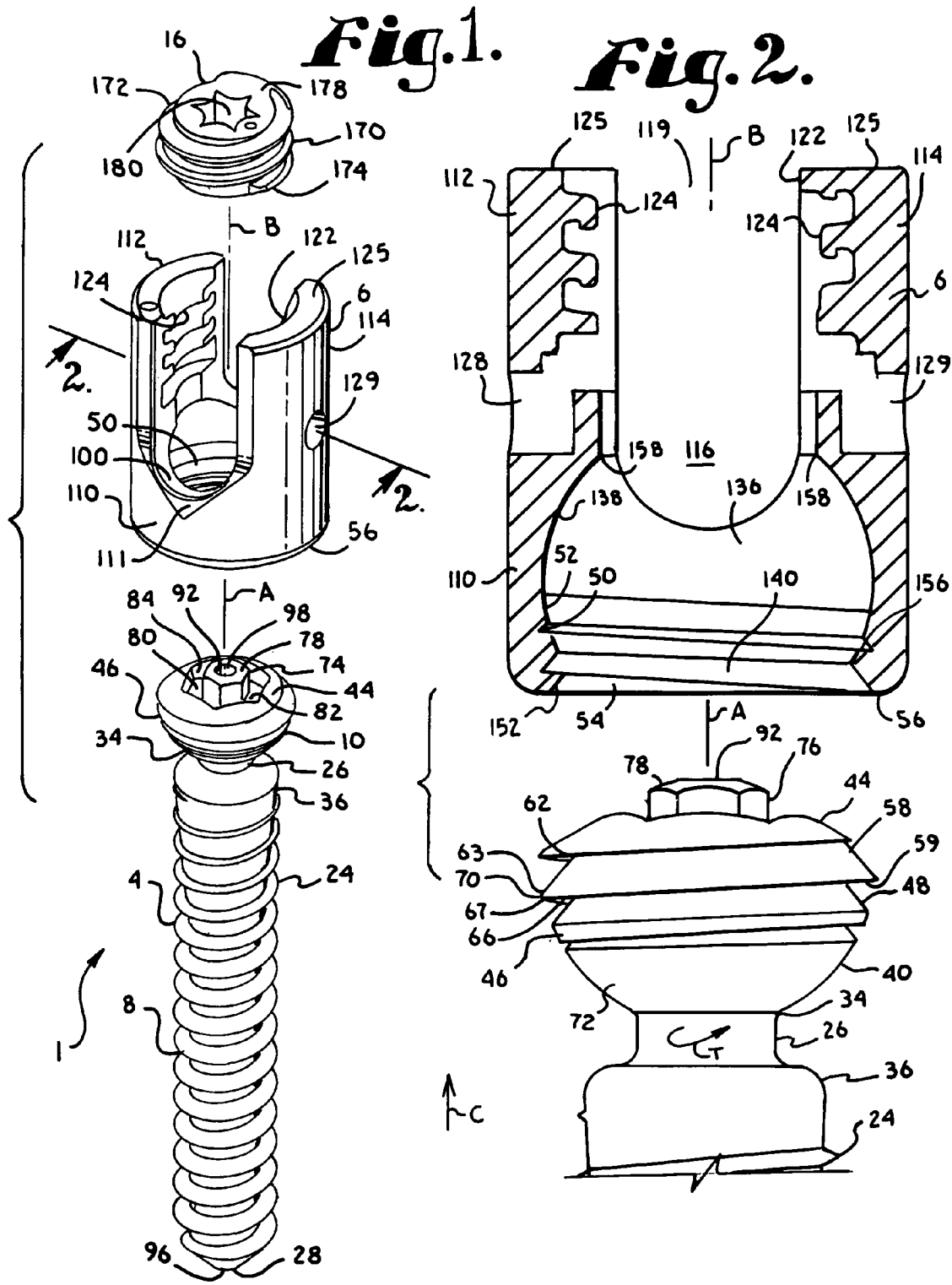

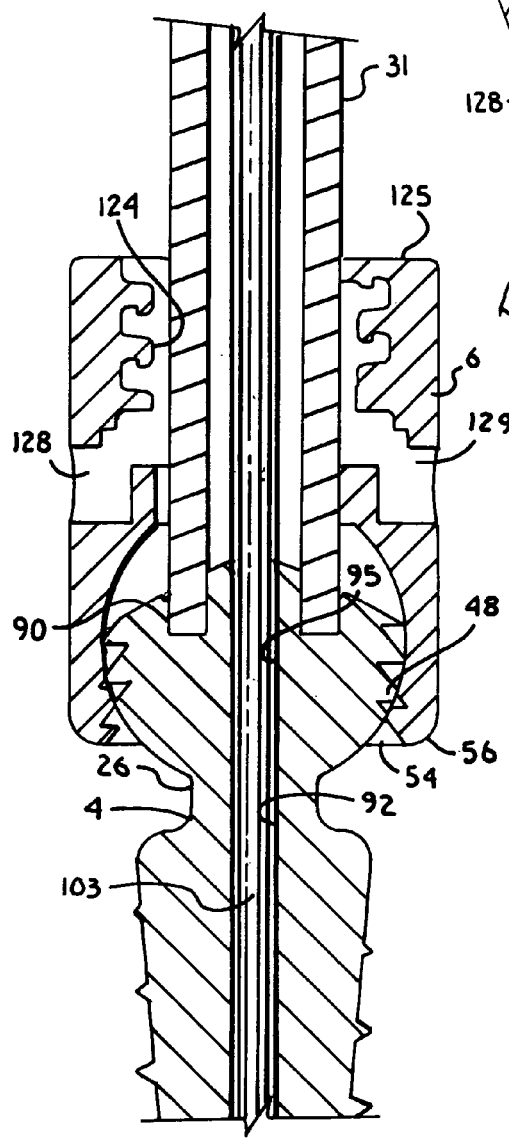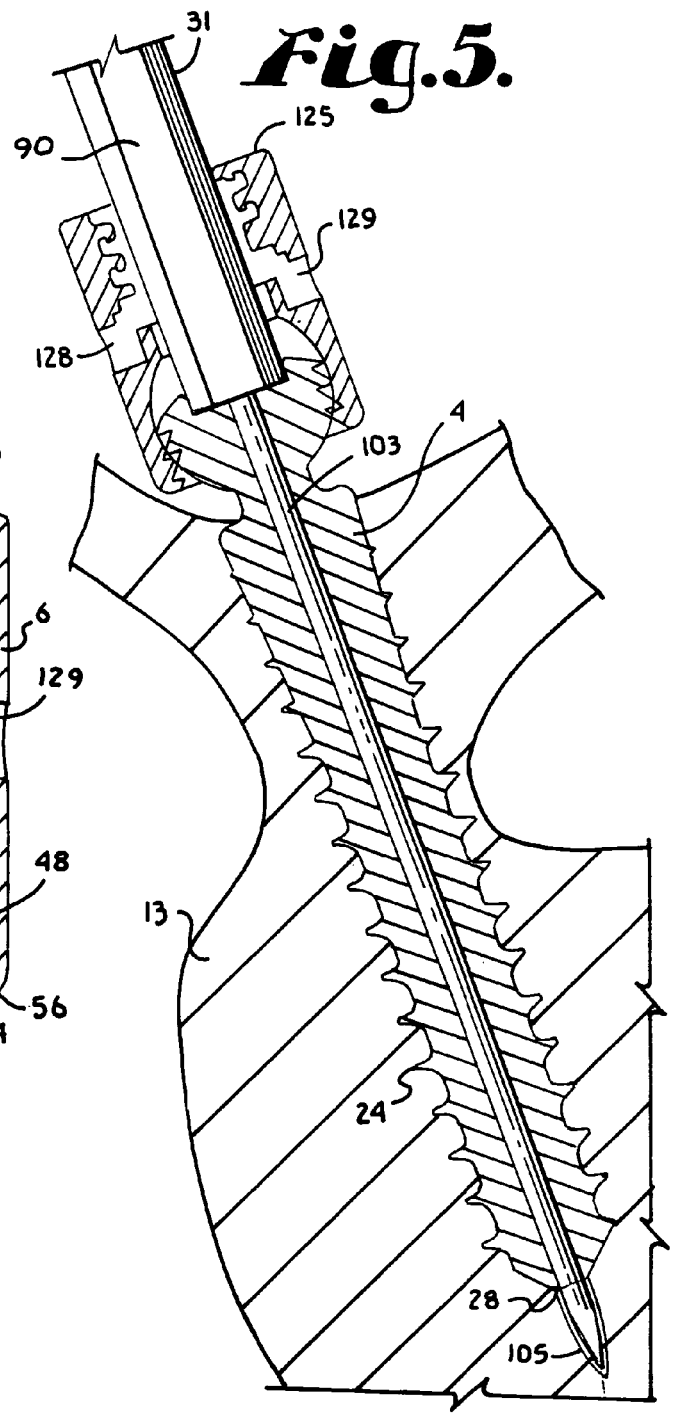

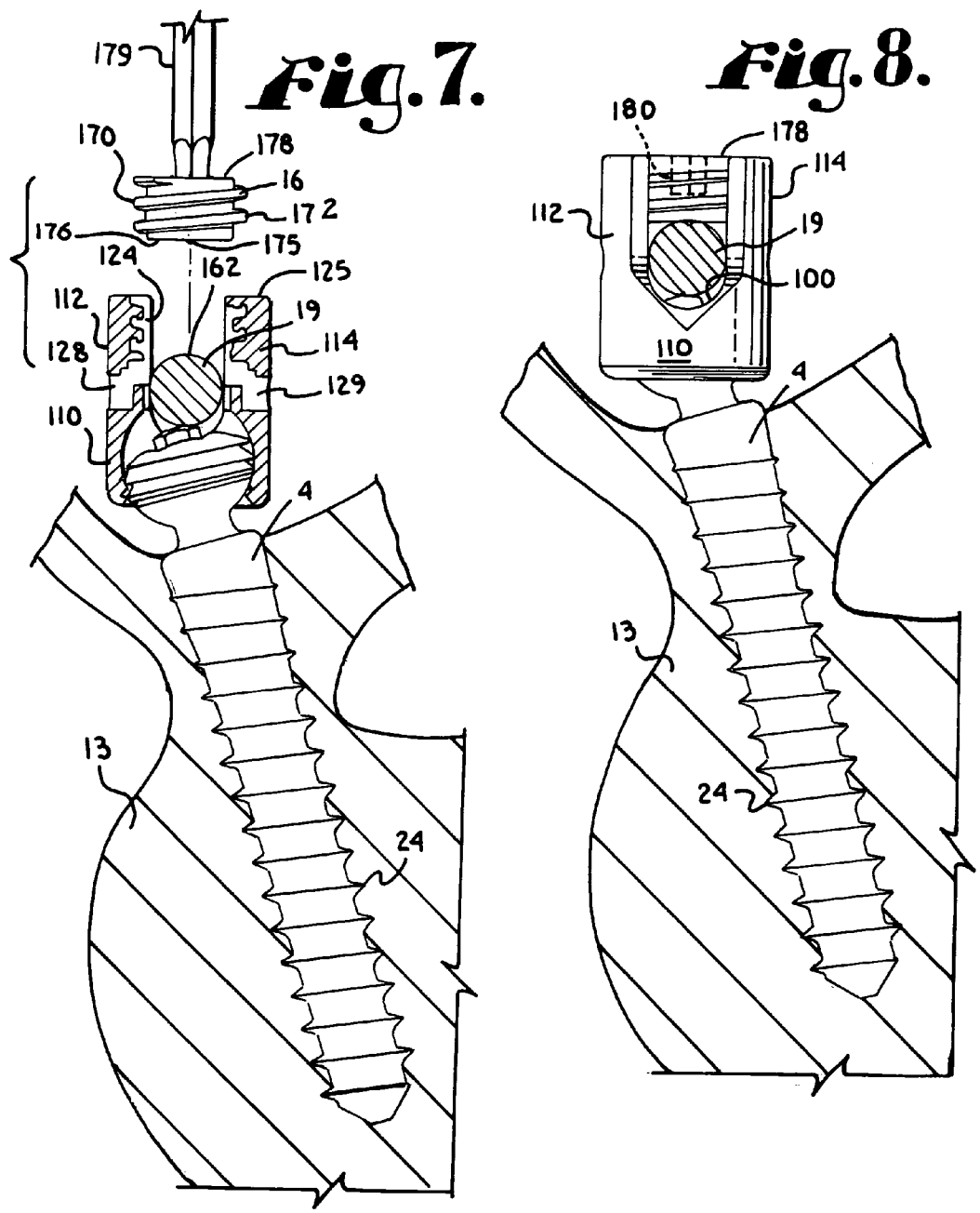

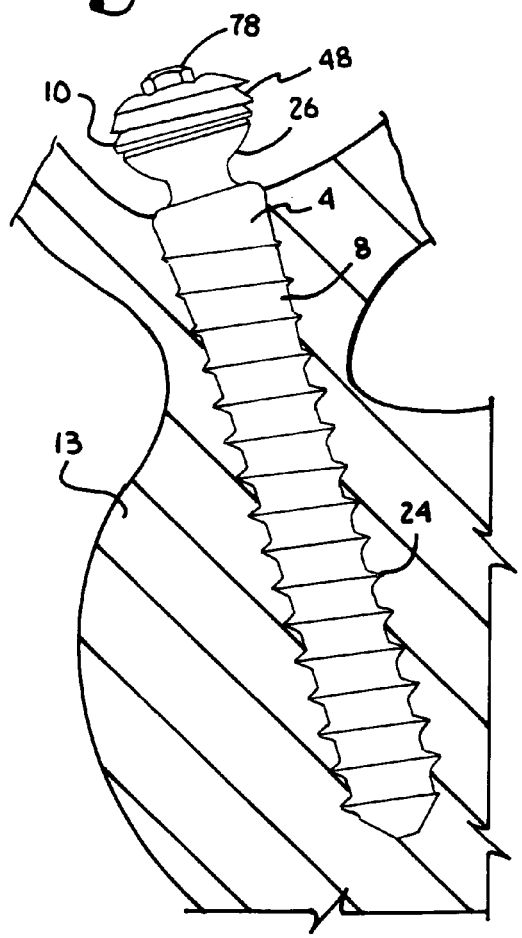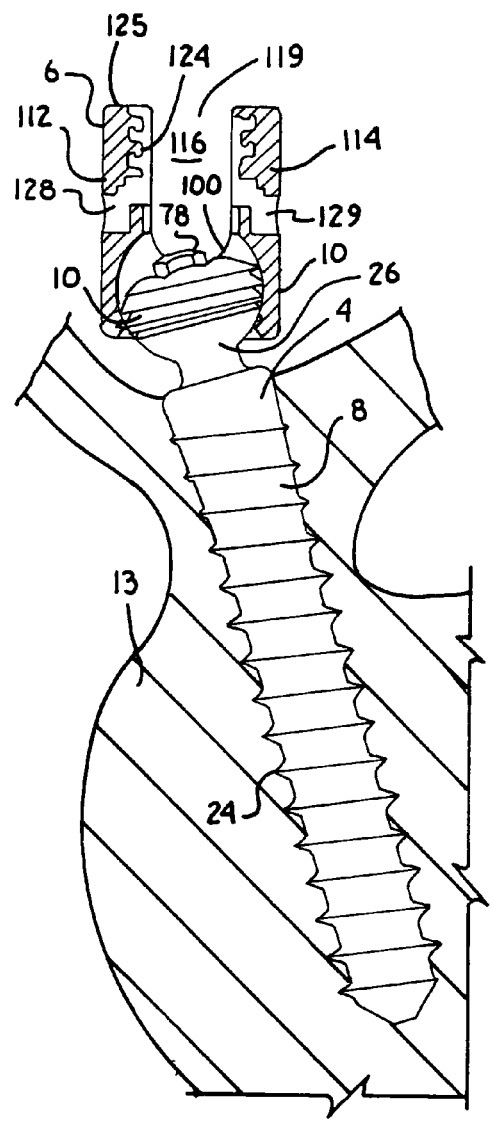

POLYAXIAL BONE SCREW WITH UPLOADED THREADED SHANK AND METHOD OF ASSEMBLY AND USE

CROSS REFERENCE TO RELATED APPLICATIONS

The present application is a continuation-in-part of U.S. application Ser. No. 10/409,935, filed Apr. 9, 2003, now Pat. No. 6,964,666.

BACKGROUND OF THE INVENTION

The present invention relates to apparatuses and methods for use in performing spinal surgery and, in particular, to polyaxial bone screws for use in spinal surgery. Such screws have a head that can swivel about a shank of the bone screw, allowing the head to be positioned in any of a number of angular configurations relative to the shank.

Bone screws are utilized in many types of spinal surgery in order to secure various implants to vertebrae along the spinal column. Spinal implant screws typically have a shank that is threaded and configured for implantation into a pedicle or vertebral body of a vertebra. Such a screw also includes a head designed to extend beyond the vertebra and also defines a channel to receive a rod or other implant. In bone screws of this type, the head may be open, in which case a closure member must be used to close between opposite sides of the head once a rod or other implant is placed therein. Alternatively, the head may be closed, wherein a rod-like implant is threaded through the head of the bone screw.

When the head and shank of the bone screw are fixed in position relative to each other, it is not always possible to insert a bone screw in such a manner that the head will be in the best position for receiving other implants. Consequently, swivel head bone screws have been designed that allow the head of the bone screw to rotate or swivel about an upper end of the shank of the bone screw while the surgeon is positioning other implants and finding the best position for the bone screw head. However, once the surgeon has determined that the head is in the best position, it is then necessary to lock or fix the head relative to the shank. Different types of structures have been previously developed for such purpose.

Because bone screws are for placement within the human body, it is desirable for the implant to have as little effect on the body as possible. Consequently, heavy, high profile, bulky implants are undesirable and lighter implants with a relatively small profile both in height and width are more desirable. However, a drawback to smaller, lighter implants is that they may be more difficult to rigidly fix in position relative to each other and in a desired position. Reduced bulk may also reduce strength, resulting in slippage under high loading. Also, more component parts may be required to rigidly fix the implant in a desired position. A further drawback of smaller components is that they may be difficult to handle during surgery because of their small size, failing to provide adequate driving or gripping surfaces for tools used to drive the shank into bone.

One undesirable attribute of some of the swivel-head implants is the need for a multitude of components that may loosen or even disassemble within the body. It is most often undesirable for components to become moveable in the body after the completion of surgery. Loosening of components relative to each other may result in related undesirable movement of the bone or vertebra that the implant was intended to stabilize.

SUMMARY OF THE INVENTION

A polyaxial bone screw assembly according to the present invention includes an elongate shank having a lower threaded body for fixation to a bone. The shank further has an upper capture structure connected to the threaded body by a neck. The capture structure has an upper end or top and a lower surface. The capture structure has a radially outward surface with a first helically wound guide and advancement structure thereon. The helically wound guide and advancement structure has a major diameter (passing through the crests) that is larger than a diameter of the aperture into which the capture structure is inserted.

The assembly also includes a head having a base with an inner surface defining a cavity. The cavity opens onto a bottom of the head through a neck opening or aperture with a portion of the inner surface defining the opening having a second helically wound guide and advancement structure sized and shaped to rotatingly mate with the first guide and advancement structure of the capture structure.

The capture structure screws upwardly into the head so as to be disposed within the cavity and captured by the head upon mating and operable rotation of the first guide and advancement structure with respect to the second guide and advancement structure until the first guide and advancement structure fully enters the cavity and becomes disengaged from the second guide and advancement structure. The capture structure is then disposed in the head cavity and free to rotate or swivel relative to the head.

The capture structure has a first orientation wherein the capture structure is within the cavity and the shank body is freely swivelable relative to the head. In a second orientation, the capture structure is in a non-mated, frictional engagement with the second guide and advancement structure and the shank body is in a fixed position with respect to the head, resulting from a force being applied to the top of the capture structure.

Preferably according to the invention, the first and second guide and advancement structures are first and second threads. Most preferably according to the invention, inverted buttress threads are utilized, although square threads, reverse angle threads and other similar mating structures can be utilized.

Also according to the invention, the elongate shank has a first axis and the head has a second axis. The first and second guide and advancement structures are configured to enter into frictional engagement when the capture structure is urged downwardly against the base neck without rotation. The capture structure may expand in response to downward pressure, further frictionally engaging and locking the first and second guide and advancement structures.

Further according to the invention, a polyaxial bone screw capture structure may include a tool engagement formation disposed at or near the top of the capture structure. Preferably, the tool engagement formation has a projection and a recessed tool seating surface with a bottom and an outer wall. Both the bottom and outer wall are sized and shaped to receive and frictionally engage with a driving tool, such as a socket tool, engaged with the tool engagement projection for driving the shank body into bone. However, other structure for driving the shank body can be used, such as off axis apertures into the threaded hemisphere.

A method according to the invention includes the steps of attaching a bone screw shank to a head by mating a first helically wound guide and advancement structure disposed on an upper portion of the bone screw shank with a second helically wound guide and advancement structure of the head to guide and advance the shank into the head until the first guide and advancement structure becomes disengaged from the second guide and advancement structure with the capture structure or upper portion slidingly received and captured in a cavity of the head. Another method step includes driving the shank body into bone by rotating the shank body with a tool engaged with a tool engagement formation disposed on or in the capture structure. The step of driving the shank into bone may take place after or before the step of mating the bone shank with the head.

OBJECTS AND ADVANTAGES OF THE INVENTION

Therefore, it is an object of the present invention to overcome one or more of the problems with polyaxial bone screw assemblies described above. An object of the invention is to provide a shank that rotatably uploads into a cavity in a head of the screw and that utilizes frictional contact of threads under pressure to fix the head relative to the shank once a desired configuration is acquired. Another object of the invention is to provide a polyaxial bone screw with features that present frictional or gripping surfaces, planar surfaces, internal apertures or the like for bone implantation tools and may be readily and securely fastened to each other as well as to the bone. Also, if part of the implant should slip relative to another part or become loose for some reason, an object of the invention is to provide an implant wherein all of the parts remain together and do not separate. Furthermore, it is an object of the invention to provide a lightweight, reduced volume, low profile polyaxial bone screw that assembles in such a manner that the components cooperate to create an overall structure that prevents unintentional disassembly. Furthermore, it is an object of the invention to provide apparatus and methods that are easy to use and especially adapted for the intended use thereof and wherein the tools are comparatively inexpensive to produce.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a polyaxial bone screw assembly according to the present invention having a shank with a capture structure at an end thereof, a head, and a closure structure.

FIG. 2 is an enlarged and fragmentary view of the assembly of FIG. 1, showing the head in cross-section, taken along the line 2-2 of FIG. 1, and illustrating the shank in front elevation prior to the insertion of the shank capture structure into the head according to a method of the invention.

FIG. 5 is a reduced and fragmentary cross-sectional view of the head and the attached shank of FIG. 4, and further showing the shank being implanted into a vertebra using a driving tool mounted on the shank capture structure.

FIG. 6 is an enlarged and fragmentary cross-sectional view of the head, shank and driving tool of FIG. 5.

FIG. 7 is a reduced and fragmentary cross-sectional view of the head, similar to FIG. 5, showing the shank in front elevation and implanted in the vertebra, a rod, in cross-section, disposed in the head, and illustrating the insertion of the closure structure using a driver.

FIG. 8 is a reduced front-elevational view of the assembly of FIG. 1, shown with a rod in cross-section, the shank implanted in the vertebra and with the closure structure fully installed.

FIG. 10 is a front-elevational view of the shank of FIG. 1 shown implanted in a vertebra (shown in cross-section) according to an alternative method of the invention.

FIG. 11 is a front-elevation view of the shank of FIG. 10, and including a reduced cross-sectional view of the head of FIG. 2, illustrating insertion of the head on the implanted shank according to an alternative method of the invention.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 3:
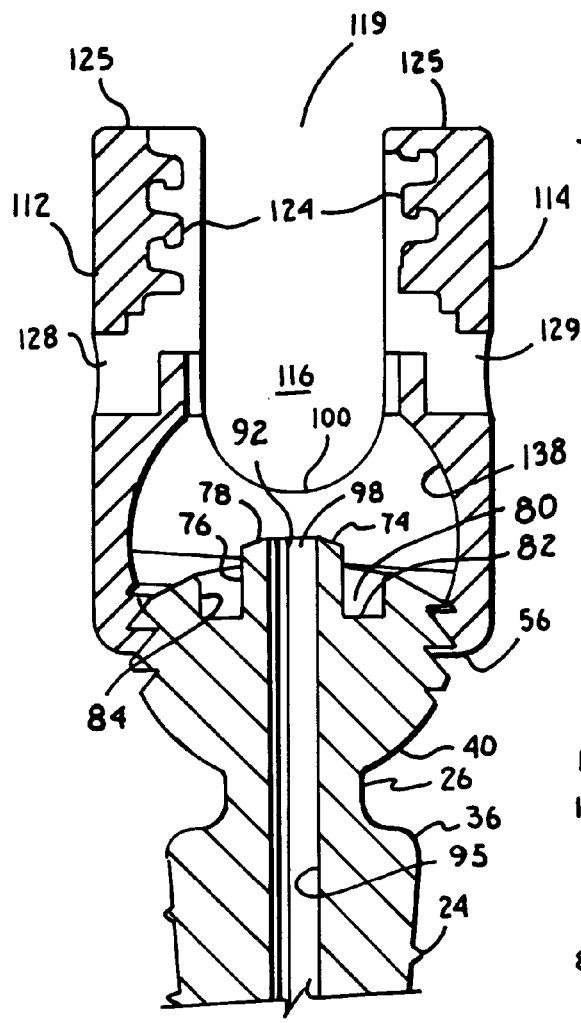
FIG. 3 is a reduced and fragmentary cross-sectional view of the head and shank, taken along the line 2-2 of FIG. 1, showing the shank capture structure partially screwed into the head.
Figure 4:
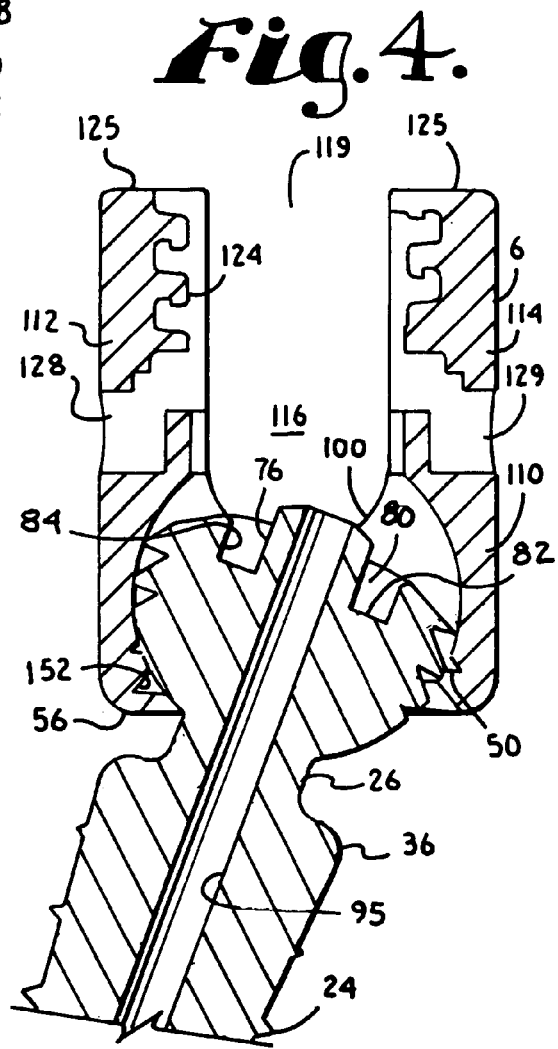
FIG. 4 is a reduced and fragmentary cross-sectional view of the head and shank of FIG. 3, illustrating the shank capture structure disposed and rotatable within the head.

With reference to FIGS. 1-9, the reference number 1 generally represents a polyaxial bone screw apparatus or assembly according to the present invention. The assembly 1 includes a shank 4 and a head 6. The shank 4 further includes a body 8 integral with an upwardly extending capture structure 10. The shank 4 and head 6 are often assembled prior to implantation of the shank body 8 into a vertebra 13, as seen in FIGS. 3 and 4. However, in a method of the invention shown in FIGS. 10 and 11, the shank body 8 is first implanted in the vertebra 13, followed by joining the head 6 to the shank 4.

FIG. 1 further shows a closure structure 16 of the invention for biasing a longitudinal member such as a rod 19 against the capture structure 10 which in turn biases the structure 10 into fixed frictional contact with the head 6, so as to fix the rod 19 relative to the vertebra 13. The head 6 and shank 4 cooperate in such a manner that the head 6 and shank 4 can be secured at any of a plurality of angles, articulations or rotational alignments relative to one another and within a selected range of angles both from side to side and from front to rear, to enable flexible or articulated engagement of the head 6 with the shank 4 until both are locked or fixed relative to each other near an end of an implantation procedure.

With reference to FIGS. 1 and 2, the shank 4 is elongate, with the shank body 8 having a helically wound bone engaging thread 24 extending from near a neck 26 located adjacent to the capture structure 10 to near a tip 28 of the body 8 and projecting radially outward therefrom.

During use, rotation of the body 8 utilizes the thread 24 for gripping and advancement in the bone and is implanted into the vertebra 13 leading with the tip 28 and driven down into the vertebra 13 with an installation or driving tool 31, so as to be implanted in the vertebra 13 to near the neck 26, as shown in FIG. 5 and as is described more fully in the paragraphs below.

The shank 4 has an elongate axis of rotation generally identified by the reference letter A. It is noted that any reference to the words top, bottom, up and down, and the like, in this application refers to the alignment shown in the various drawings, as well as the normal connotations applied to such devices, and is not intended to restrict positioning of the assembly 1 in actual use.

The neck 26 extends axially outward and upward from the shank body 8 to a base 34 of the capture structure 10. The neck 26 generally has a reduced radius as compared to an adjacent top 36 of the shank body 8. Further extending axially and outwardly from the neck 26 is the capture structure 10 that provides a connective or capture apparatus disposed at a distance from the body top 36 and thus at a distance from the vertebra 13 when the shank body 8 is implanted in the vertebra 13.

The capture structure 10 is configured for connecting the shank 4 to the head 6 and then capturing the shank 4 in the head 6. The capture structure 10 has an outer substantially hemi-spherically or partial spherically shaped surface 40 extending from the base 34 to a top portion 44. Formed on an upper part 46 of the surface 40 is a guide and advancement structure illustrated in the drawing figures as an inverted or reverse buttress thread 48. The thread 48 is sized and shaped to mate with a cooperating guide and advancement structure 50 disposed on an inner surface 52 of the head 6 disposed adjacent to and defining an opening 54 of a lower end or bottom 56 of the head 6. Preferably, the thread 48 is relatively thick and heavy to give strength to the thread and prevent the threads from being easily bent or deformed when axial pressure is applied to the shank 4 to maintain the capture structure 10 in the head 6, as described further below.

The thread 48 winds about the upper portion 46 in a generally helical pattern or configuration that is typical of threads and can have various pitches, be clockwise or counterclockwise advanced, or vary in most of the ways that conventional buttress threads vary. The thread 48 has a leading surface or flank 58 and a trailing surface or flank 59. As used herein, the terms leading and trailing refer to the direction of advancement of the capture structure 10 into the guide and advancement structure 50 of the head 6 aligning the axis A of the shank 4 with an elongate axis of rotation B of the head 6 and directing the capture structure 10 toward the head 6, as shown by the straight arrow C illustrated in FIG. 2.

The leading surface 58 has an inner edge 62 and an outer edge 63. The trailing surface 59 has an inner edge 66 and an outer edge 67. At the crests of the thread 48, where the leading surface outer edge 63 and the trailing surface outer edge 67 meet or are closely spaced relative to one another, preferably there is a slight relief as shown in the drawings so as to have a slight connecting wall or crest surface 70 therebetween along a substantial length of the thread that decreases the sharpness of the buttress thread 48 and increases the strength and surface contact thereof. The size of the crest or connecting surface 70 varies, generally increasing as the thread 48 winds from the top surface 44 to a non-threaded lower portion 72 of the surface 40.

As can be seen in the drawing figures, the general shape of the cross section of the thread 48 is that of a right triangle, with the leading surface 58 sloping away from the axis A and downwardly from the inner edge 62 and the trailing surface 59 extending substantially horizontally from the inner edge 66 and thus substantially perpendicular to the axis A.

Although a reverse or inverted buttress thread as described herein is preferable for use according to the invention, it is foreseen that other thread types, such as V-threads, square threads, other inverted thread types or other thread like or non-thread like guide and advancement structures, such as flange form, helically wound advancement structures may be utilized according to the invention. Other preferred threadtypes also include square threads with wide strong teeth and greater surface contact as well as modified inverted buttress threads, for example buttress threads wherein the angular relationship between the trailing and leading surfaces are modified somewhat, or wherein the size, shape or orientation of the connecting wall between the leading and trailing surfaces is modified somewhat.

Advancement of the capture structure 10 into the head 6 is accomplished by rotating the shank 4 in a counterclockwise direction about the axes A and B and into the head 6 as illustrated by the arrow T in FIG. 2. As will be described more fully below, an outer edge of the trailing surface or flank 59 and/or the connecting surface 70 may also be a loading surface after the capture structure 10 is fully disposed in the head 6.

Figure 9:
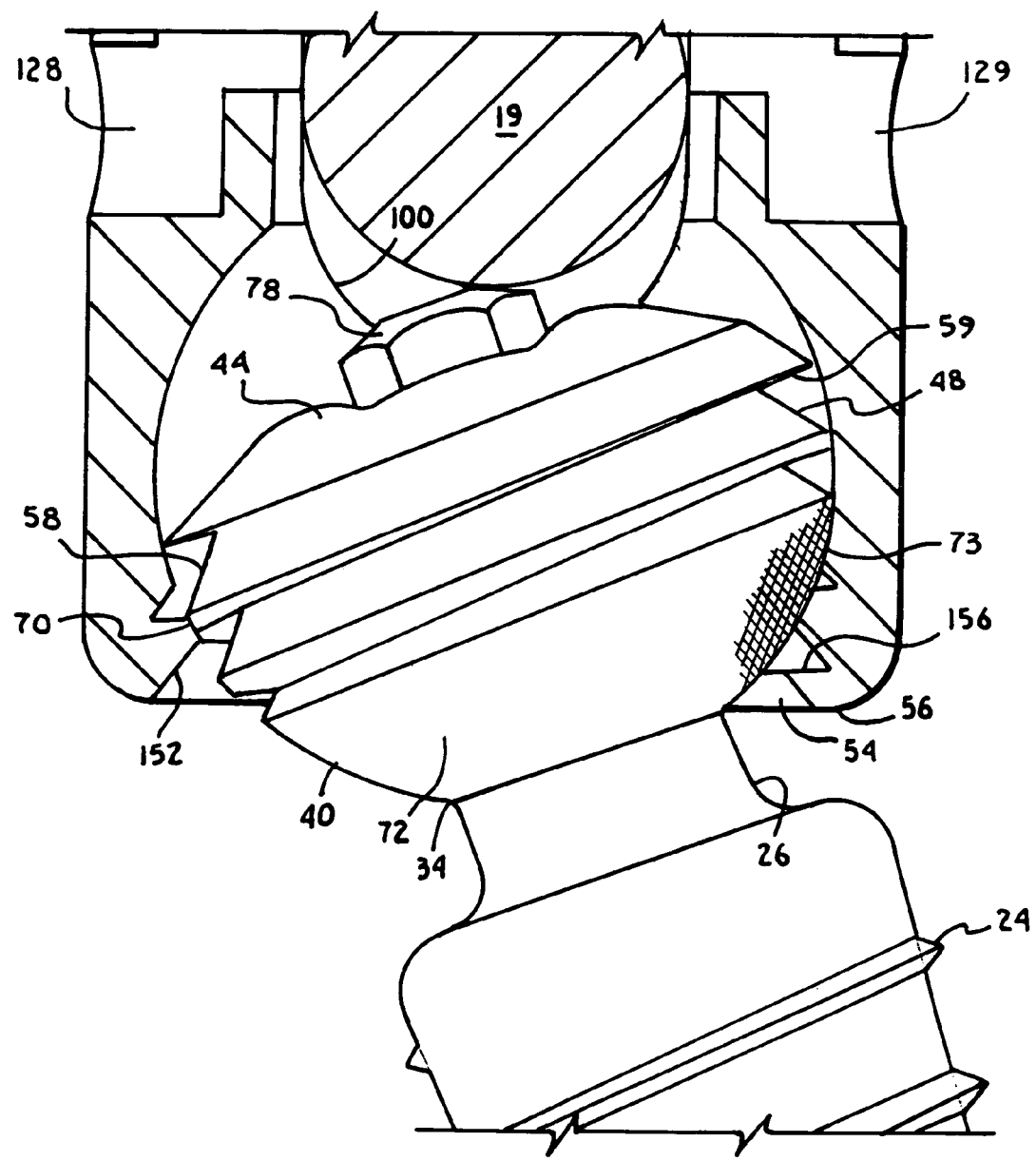
FIG. 9 is an enlarged and fragmentary view of the assembly of FIG. 8 with the head and rod in cross-section, showing the details thereof.

The non-threaded lower portion 72 of the capture structure 10 surface 40 that is disposed between the base 34 and the thread 48 may have a smooth or a high-friction or roughened surface, such as a scored or knurled surface 73 illustrated on FIG. 9. As also illustrated in FIG. 9 and will be described more fully below, the lower portion 72 may come into contact with the head guide and advancement structure 50 during a rod reduction process according to the present invention.

In the embodiment shown, the shank 4 further includes a rod and tool engagement structure 74 projecting upwardly from the top portion 44 of the capture structure 10. The tool engagement structure 74 has a hexagonally shaped head 76 with a substantially domed top. 78. The structure 74 is coaxial with both the threaded shank body 8 and the capture structure 10. The head 76 is sized and shaped for engagement with the driving tool 31 shown in FIGS. 5 and 6 that includes a driving and mating structure in the form of a socket. The tool 31 is configured to fit about the head 76 so as to form a socket and mating projection for both operably driving and rotating the shank body 8 into the vertebra 13.

In the embodiment shown, to provide further mechanical advantage during installation of the shank 4 into the vertebra 13, the capture structure 10 includes a counter-sunk portion 80 formed in the top 44, the portion 80 adjacent to and surrounding the head 76. The portion 80 includes a planar seating surface 82 disposed perpendicular to the axis A and spaced from the top portion 44. Contiguous to both the surface 82 and the top 44 are faces 84 that are disposed parallel to the axis A and thus are substantially perpendicular to the surface 82. The faces 84 form a hex-shaped outer periphery of the counter-sunk portion 80. The tool 31 includes an outer surface portion 90 sized and shaped to mate with the bottom and both side walls of the counter-sunk portion 80, such that a bottom of the tool 31 seats on the surface 82 and the outer surface portion 90 is adjacent to and engaging the faces 84 when the tool 31 is disposed about and engaging with the hexagonally shaped head 76.

The domed top end surface 78 of the shank 4 is preferably convex, curved or dome-shaped as shown in the drawings, for positive engagement with the rod 19 when the bone screw assembly 1 is assembled, as shown in FIGS. 7-9, and in any alignment of the shank 4 relative to the head 6. In certain embodiments, the surface 78 is smooth. While not required in accordance with the practice of the invention, the surface 78 may be scored or knurled to further increase frictional engagement between the dome 78 and the rod 19. The dome 78 may be radiused so that the dome 78 engages the rod 19 slightly above a surface 100 defining a lower portion of a rod receiving channel in the head 6, even as the head 6 is swivelled relative to the shank 4 so that pressure is always exerted on the dome surface 78 by the rod 19 when the assembly 1 is fully assembled. It is foreseen that in other embodiments the dome 78 can have other shapes which may include off-axis apertures for driving the shank with a mating tool.

The shank 4 shown in the drawings is cannulated, having a small central bore 92 extending an entire length of the shank 4 along the axis A. The bore 92 is defined by an inner substantially cylindrical wall 95 of the shank 4 and has a first circular opening 96 at the shank tip 28 and a second circular opening 98 at the top domed surface 78. The bore 92 is coaxial with the threaded body 8 and the capture structure 10. The bore 92 provides a passage through the shank 4 interior for a guide pin or length of wire 103 inserted into a small pre-drilled tap bore 105 in the vertebra 13 prior to the insertion of the shank body 8, the pin 103 providing a guide for insertion of the shank body 8 into the vertebra 13.

The head 6 is partially cylindrical in external profile and includes a base portion 110 extending from the end 56 to a V-shaped surface 111 disposed at a periphery of the surface 100 and extending radially outwardly and downwardly therefrom. The base 110 is integral with a pair of upstanding and spaced arms 112 and 114. The surface 100 and the arms 112 and 114 forming a U-shaped channel 116 between the arms 112 and 114 with an upper opening 119. The lower surface 100 defining the channel 116 preferably has substantially the same radius as the rod 19. In operation, the rod 19 preferably is located just above the channel lower surface 100, as shown in FIGS. 7-9.

Each of the arms 112 and 114 has an interior surface 122 that defines an inner cylindrical profile and includes a discontinuous helically wound guide and advancement structure 124 beginning at a top 125 of the head 6 and extending downwardly therefrom. The guide and advancement structure 124 is a partial helically wound flange-form configured to mate under rotation about the axis B with a similar structure disposed on the closure structure 16, as described more fully below. However, it is foreseen that the guide and advancement structure 124 could alternatively be a V-shaped thread, a buttress thread, a reverse angle thread or other thread-like or non-thread-like helically wound guide and advancement structure for operably guiding under rotation and advancing the closure structure 16 between the arms 112 and 114, as well as eventual torquing when the closure structure 16 abuts against the rod 19.

The head 6 includes external, grip bores 128 and 129 disposed on the respective arms 112 and 114 for positive engagement by a holding tool (not shown) to facilitate secure gripping of the head 6 during assembly of the head 6 with the shank 4. Furthermore, the grip bores 128 and 129 may be utilized to hold the head 6 during the implantation of the shank body 8 into the vertebra 13. The bores 128 and 129 are centrally located on the respective arms 112 and 114 and may communicate with upwardly projecting hidden recesses to further aid in securely holding the head 6 to a holding tool (not shown). It is foreseen that the bores 128 and 129 may be configured to be of a variety of sizes, shapes and locations along outer surfaces of the arms 112 and 114.

Communicating with the U-shaped channel 116 of the head 6 is a chamber or cavity 136 substantially defined by a partially spherical inner surface 138 that is disposed in the base portion 110 of the head beneath the interior cylindrical surface 122 of the arms 112 and 114 and extending into the inner surface 52 that defines the guide and advancement structure 50. The cavity 136 communicates with both the U-shaped channel 116 and a bore 140 that also is defined by the guide and advancement structure 50, that in turn communicates with the opening 54 at the bottom 56 of the head 6.

The guide and advancement structure 50 includes a leading surface 152 and a trailing surface 156. Similar to what is described herein with respect to the reverse buttress thread 48 of the capture structure 10, the guide and advancement structure 50 is preferably of a buttress thread type as such structure provides strength and stability to the assembly 1, with the trailing surface 156 that extends substantially perpendicular to the axis B. The cross-sectional configuration of an inverted buttress thread also results in an orientation for the structure 50 that improves strength and desirably resists pushing of the capture structure 10 out of the opening 54. However, as with the thread 48, it is foreseen that other types of threaded and non-threaded helical structures may be utilized in accordance with the present invention.

A juncture of the interior surface 122 and the cavity inner surface 138 forms an opening or neck 158 that has a radius extending from the Axis B that is smaller than a radius extending from the Axis B to the inner surface 138. Also, a radius from the lower opening 54 to the Axis B is smaller than the radius extending from the Axis B to the inner surface 138 and the inner surface portion 52 defining the guide and advancement structure 50. Thus, the cavity or chamber 136 is substantially spherical, widening and opening outwardly and then inwardly in a direction toward the lower opening 54. However, it is foreseen that other shapes, such as a cone or conical shape, may be utilized for a head inner cavity according to the invention.

After the reverse buttress thread 48 of the capture structure 10 is mated and rotated to a position within the cavity 136 and further upwardly and axially into non-engagement beyond the trailing surface 156 of the guide and advancement structure 50, the capture structure 10 is rotatable or swingable within the cavity 136 until later frictionally locked in place, and cannot be removed from the head 6 through the upper neck 158 or through the lower bore 140 without reversing the assembly process with the components in axial alignment. As shown in FIG. 4, the capture structure 10 is held within the cavity 136 from above by the partially spherical surface 138 and from below by the threaded inner surface 52. Stated in another way, the thick strong thread 50 of the head 6 disposed along the surface 52, and the unmated, thick strong thread 48 of the capture structure 10, prevent the capture structure 10 from being pushed or pulled from the chamber 136, unless the capture structure 10 is rotated and unscrewed therefrom again through the bore 140 in axial alignment. More specifically, the buttress thread 48, particularly the trailing surface 59, resists pushing out of the bore 140 and bottom opening 54 due to the strength and orientation of the buttress thread and the fact that the greatest diameter of the threaded portion 46 of the capture structure 10 is greater than the interior diameter of the bore 140.

As shown in FIG. 9 and described more fully below, the buttress thread 48 and mating thread 50 further provide a frictional interface when pushed from above, as by a closure structure 16 pushing on a rod 19 or other tool pushing against the dome 78, with outer edges of the thread 48 contacting the inner surface 52 or portions of the thread 50, resulting in a digging or abrasion into the surface 52 by the thread 48. However, if there is no pushing from above, the cavity or chamber 136 allows the structure 10 to freely rotate in the chamber 136 to a position or orientation desired by a surgeon. In this manner, the head 6 is able to swivel or swing about the shank 4 until subsequently locked in place.

The elongate rod or longitudinal member 19 that is utilized with the assembly 1 can be any of a variety of implants utilized in reconstructive spinal surgery, but is normally a cylindrical elongate structure having a cylindrical surface 162 of uniform diameter and preferably having a generally smooth surface. The rod 19 is also preferably sized and shaped to snugly seat near the bottom of the U-shaped channel 116 of the head 6 and, during normal operation, is positioned slightly above the bottom of the channel 116 near, but spaced from, the lower surface 100.

In particular, the rod 19 normally directly or abuttingly engages the shank top surface 78, as shown in FIGS. 8 and 9 and is biased against the dome shank top surface 78, consequently biasing the shank 4 downwardly in a direction toward the base 110 of the head 6 when the assembly 1 is fully assembled with the rod 19 and the closure member 16. For this to occur, the shank top surface 78 must extend at least slightly into the space of the channel 116, above the surface 100 when the capture structure 10 is snugly seated in the lower part of the head cavity 136 as shown in FIG. 9 with a portion of the buttress thread 48 contacting a portion of the structure 50, resulting in a frictional interface between the thread 48 and the thread 50. The pressure placed on the capture structure 10 by the rod 19 and closure member 16 may also cause a spreading or expansion of the capture structure 10, causing an interlocking or interdigitation of the threads 48 and 50, or an abrading of the surface 52 at the thread 50 by the thread 48. The shank 4 and the capture structure 10 are thereby locked or held in position relative to the head 6 by the rod 19 firmly pushing downward on the shank domed surface 78.

With reference to FIGS. 1, 7 and 8, the closure structure or closure top 16 can be any of a variety of different types of closure structures for use in conjunctions with the present invention with suitable mating structure on the upstanding arms 112 and 114. The closure top 16 screws between the spaced arms 112 and 114 and closes the top of the channel 116 to capture the rod 19 therein.

The illustrated closure top 16 has a generally cylindrically shaped body 170, with a helically wound guide and advancement structure 172 that is sized, shaped and positioned so as to engage the guide and advancement structure 124 on the arms 112 and 114 to provide for rotating advancement of the closure structure 16 into the head 6 when rotated clockwise and, in particular, to cover the top or upwardly open portion of the U-shaped channel 116 to capture the rod 19, preferably without splaying of the arms 112 and 114. The body 170 further includes a base or bottom 174 having a pointed rod engaging projection or point 175 extending or projecting axially beyond a lower rim 176. The closure structure 16, with the projection 175 frictionally engaging and abrading the rod surface 162, thereby applies pressure to the rod 19 under torquing, so that the rod 19 is urged downwardly against the shank domed surface 78 that extends into the channel 116. Downward biasing of the shank surface 78 operably produces a frictional engagement between the rod 19 and the surface 78 and also urges the capture structure 10 toward the base 110 of the head 6, as will be described more fully below, so as to frictionally seat the capture structure buttress thread 48 and/or lower portion 72 against the threaded inner surface 52 of the head 6, also fixing the shank 4 and capture structure 10 in a selected, rigid position relative to the head 6.

The illustrated closure structure 16 further includes a substantially planar top surface 178 that has a centrally located, hexalobular internal driving feature 180 formed therein (sold under the trademark TORX), which is characterized by an aperture with a 6-point star-shaped pattern. It is foreseen that other driving features or apertures, such as slotted, hex, tri-wing, spanner, and the like may also be utilized according to the invention. With reference to FIG. 7, a driving/torquing tool 179 having a cooperating hexalobular driving head is used to rotate and torque the closure structure 16. The tool 179 may also be utilized for removal of the closure structure 16, if necessary.

It is foreseen that a closure structure according to the invention may be equipped with a break-off feature or head, the closure structure sized and shaped to produce a break-way region that breaks at a preselected torque that is designed to properly seat the closure structure in the head 6. Such a closure structure would include removal tool engagement structure, such as a pair of spaced bores, a countersunk hex-shaped aperture, a left hand threaded bore, or the like, fully accessible after the break-off head feature breaks away from a base of the closure structure.

In use, prior to the polyaxial bone screw assembly 1 being implanted in a vertebra according to the invention, the shank capture structure 10 is often pre-loaded by insertion or bottom-loading into the head 6 through the opening 54 at the bottom end 56 of the head 6. The capture structure 10 is aligned with the head 6, with the axes A and B aligned so that the reverse buttress thread 48 of the capture structure 10 is inserted into and rotatingly mated with the guide and advancement structure 50 on the head 6. The shank 4 is rotated in a counter-clockwise direction as illustrated by the arrow T in FIG. 2 to fully mate the structures 48 and 50, as shown in FIG. 3, and the counter-clockwise rotation is continued until the thread 48 disengages from the thread 50 and the capture structure 10 is fully disposed in the head cavity 136.

In the position shown in FIG. 4, the shank 4 is in slidable and rotatable engagement with the head 6, while the capture structure 10 is maintained in the head 6 with the shank body 8 in rotational relation with the head 10. For example, an extent of rotation is shown in FIGS. 4 and 9 where it can be deduced that the shank body 8 can be rotated through a substantial angular rotation relative to the head 6, both from side to side and from front to rear so as to substantially provide a universal or ball joint wherein the angle of rotation is only restricted by engagement of the thread 48 of the capture structure 10 and the thread 50 of the head 6 at a lower portion or area of the head 6 and by the thread 48 contacting the inner spherical surface 138 of the head 6 at an upper portion or area of the head 6.

With reference to FIGS. 5 and 6, the assembly 1 is then typically screwed into a bone, such as the vertebra 13, by rotation of the shank body 8 using the driving tool 31 that operably drives and rotates the shank 8 by engagement thereof with the hexagonally shaped extension head 76 of the shank 4. Preferably, when the driving tool 31 engages the head 76 during rotation of the driving tool 31, the outer portion 90 also engages the faces 84 and a bottom of the tool 31 is fully seated upon and frictionally engages with the planar surface 82 disposed in the counter-sunk portion 80 of the capture structure 10. It is foreseen that in other embodiments according to the invention, the counter-sunk portion may be defined by more or fewer engaging surfaces.

With particular reference to FIG. 5, the vertebra 13 may be pre-drilled with the small tap bore 105 to minimize stressing the bone and thereafter have the guide wire or pin 103 inserted therein to provide a guide for the placement and angle of the shank 4 with respect to the vertebra 13. A further tap bore (not shown) may be made using a tap with the guide pin 103 as a guide. Then, the assembly 1 is threaded onto the guide pin 103 utilizing the cannulation bore 92 by first threading the pin 103 into the bottom opening 96 and then out of the top opening 98. The shank body 8 is then driven into the vertebra 13, using the pin 103 as a placement guide.

With reference to FIGS. 7-9, the rod 19 is eventually positioned within the head U-shaped channel 116, and the closure structure or top 16 is then inserted into and advanced in a clock-wise direction between the arms 112 and 114 so as to bias or push against the rod 19. The closure structure 16 is rotated, utilizing the tool 179 in engagement with the driving feature or aperture 180 until an appropriate torque is achieved, for example 90 to 120 inch pounds, to urge the rod 19 downwardly. The shank top domed surface 78, because it is rounded to approximately equally extend upward into the channel 116 approximately the same amount no matter what degree of rotation exists between the shank 8 and the head 6 and because the surface 78 is sized to extend upwardly into the U-shaped channel 116, the surface 78 is engaged by the rod 19 and pushed downwardly toward the base 110 of the head 6 when the closure structure 16 biases downwardly toward and onto the rod 19.

In very unusual circumstances, the Axis A and the Axis B are aligned and in such a case the surface 72 of the capture structure 10 engages and sets atop the thread 50 of the head 6. Downward pressure on the shank 4 produces frictional fixing between the surface 72 and the thread 50 in such an alignment.

In most final placements, the head 6 is tilted relative to the shank 4, so that the Axes A and B are not aligned. In such a situation, downward pressure on the shank 4 in turn urges the capture structure 10 downward toward the head inner surface 52 and associated guide and advancement structure 50, with a portion of the buttress thread 48 being urged into frictional engagement with a portion of the threaded surface 52 on the head 6. Further, another portion of the thread 50 engages and frictionally locks with a portion of the capture structure surface 72, as seen in FIG. 9. As the closure structure 16 presses against the rod 19, the rod 19 presses against the shank 4, and the capture structure 10 becomes frictionally and rigidly attached to the head 10. Outer edges formed by the leading 58 and trailing 59 surfaces of the thread 48 frictionally engage and abrade the inner threaded surface 52 and the spherical surface 138. If the pressure is such that the capture structure 10 expands, a meshing and/or interlocking of the thread 48 and the thread 50 may occur. Thus, this interlocking or meshing of the surfaces of the thread 48 with the surfaces of the thread 50 further fixes the shank body 8 in a desired angular configuration with respect to the head 6 and the rod 19.

FIG. 8 illustrates the polyaxial bone screw assembly 1 with the rod 19 and the closure structure 16 positioned in a vertebra 13. The axis A of the bone shank 8 is illustrated as not being coaxial with the axis B of the head 6 and the shank body 8 is fixed in this angular locked configuration.

Other angular configurations can be achieved, as required during installation surgery due to positioning of the rod 19 or the like. With reference to FIG. 9, an implanted polyaxial bone screw assembly 1 is shown wherein the shank body 8 is fixed in a desired angular orientation with respect to the head 6 with the rod 19 in frictional contact with the domed surface 78, a portion of the wall 70 disposed between the leading surface 52 and the trailing surface 59 being in frictional contact with the thread 50 of the head 6, and a portion of the lower spherical surface 72 of the capture structure 10 in contact with the thread 50 of the head 6.

It is foreseen that, when the shank 4 is not disposed at an angle with respect to the head, in other words, when the axes A and B remain aligned and the shank body 8 is locked into a position substantially coaxial with the head, then the surface 72 abuts against the guide and advance structure 50 only. Such a locked position adequately holds the shank in place, with outer edges of the thread 50 frictionally engaging and abrading the surface 72, but as noted before, this is not common. The shank 4 typically is locked into place with a portion of the thread 48 frictionally interfacing with the thread 50. It is foreseen that according to the invention, the geometry of the surface 72 may be modified slightly so that when a coaxial orientation of the shank 4 and the head 6 is desired, the buttress thread 48 will frictionally engage with the thread 50 with no contact being made between the head 6 and the capture structure 10 at either the spherical surface 138 or the spherical surface 72.

If removal of the assembly 1 and associated rod 19 and closure structure 16 is necessary, disassembly is accomplished by using the driving tool 179 that is received in and mates with the driving feature 180 and then turned counter-clockwise to rotate the closure structure 16 and reverse the advancement thereof in the head 6. Then, disassembly of the assembly 1 is continued in reverse order to the procedure described previously herein for assembly.

With reference to FIGS. 10 and 11, in an alternative method according to the invention, the shank 4 is first implanted into the vertebra 13 by rotation of the shank 8 into the vertebra 13 using the driving tool 31 that operably drives and rotates the shank 8 by engagement thereof with the hexagonally shaped extension head 76 of the shank 4. As already described herein, when the driving tool 31 engages the head 76 during rotation of the driving tool 31, the outer portion 90 also engages the faces 84 and a bottom of the tool 31 is fully seated upon and frictionally engages with the planar surface 82 disposed in the counter-sunk portion 80 of the capture structure 10. It may be desirable to only partially implant the shank 8 into the vertebra 13, with the capture structure 10 extending proud to provide space for the attachment of the head 6 to the shank 4.

The head 6 is then attached to the shank 4 by inserting the head 6 onto the capture structure with the axes A and B aligned and mating the thread 48 with the thread 50 by rotating the head 6 in a clockwise direction. The head is then rotated until the thread 48 disengages with the thread 50 and the capture structure 10 is freely rotatably disposed in the head cavity 136. Then, the shank body the shank 4 can be further driven into the vertebra 13, if necessary, utilizing the driving tool 31 as already described herein. The remainder of the implant assembly includes elements that have been previously described.

It is to be understood that while certain forms of the present invention have been illustrated and described herein, it is not to be limited to the specific forms or arrangement of parts described and shown.

What is claimed and desired to be secured by letters patent is as follows:

1. A polyaxial bone screw assembly for implantation in a human comprising:
   a) an elongate shank having a body for fixation to a bone and a capture structure extending from the body, the capture structure having a first helically wound guide and advancement structure; and
   b) a head having an upper opening and a base with an inner surface defining a base cavity and a lower opening communicating with cavity having a second helically wound guide and advancement structure sized and shaped to rotatingly mate with the first guide and advancement structure, the capture structure being disposed and captured in the cavity upon operable mating and rotation of the first guide and advancement structure with the second guide and advancement structure until the first guide and advancement structure becomes disengaged from the second guide and advancement structure, the capture structure having a first orientation wherein the capture structure is disposed in the cavity and the shank body is swivelable relative to the head, and a second orientation, wherein the capture structure is in a non-threadedly mated frictional engagement with the second guide and advancement structure so that the shank cannot swivel relative to the head and wherein the shank capture structure can only be threadedly loaded into the cavity through the lower opening.

2. The assembly of claim 1 wherein the first and second guide and advancement structures are first and second threads.

3. The assembly of claim 2 wherein the first thread is an inverted buttress thread.

4. The assembly of claim 1 wherein a portion of the first guide and advancement structure frictionally engages with a portion of the second guide and advancement structure in said second orientation.

5. The assembly of claim 1 wherein the capture structure has a tool engagement formation disposed thereon adapted for non-slip engagement by a tool for driving the shank body into bone.

6. The assembly of claim 5 wherein the capture structure tool engagement formation is an upward axial projection having a hexagonal profile.

7. The assembly of claim 5 wherein the tool engagement formation is a projection and the capture structure has a tool seating surface, the projection and the tool seating surface partially defining a recess adapted for receiving a driving tool engaged with the tool engagement projection and wherein the driving tool is adapted to be in contact with the tool seating surface when driving the shank body into bone.

8. The assembly of claim 7 wherein the capture structure has at least one engagement wall disposed perpendicular to the tool seating surface and spaced from the projection, the engagement wall partially defining the recess for receiving the driving tool and wherein the driving tool is adapted to be in contact with the tool seating surface, the projection and the engagement wall when driving the shank body into bone.

9. The assembly of claim 1 wherein the shank is cannulated from the top to a bottom thereof.

10. The assembly of claim 1 further comprising a closure structure insertable into an upper opening of the head, the closure structure for indirectly operably urging the shank in a direction to frictionally lock the capture structure to the head in the second orientation thereof, thereby locking the shank body in a selected angle with respect to the head.

11. The assembly of claim 10 wherein the closure structure has a hexalobular internal driving feature.

12. The assembly of claim 10 wherein:
(a) the head has upstanding spaced arms defining an open channel, the arms having a third guide and advancement structure on an inside surface thereof, the channel communicating with the cavity; and
(b) the closure structure is sized and shaped to be positionable between the arms for closing the channel, the closure structure having a fourth guide and advancement structure for rotatably mating with the third guide and advancement structure, so as to be adapted to bias the closure structure upon advancement rotation against a rod disposed in the channel.

13. The assembly of claim 12 wherein the capture structure top has a dome sized and shaped to extend into the channel so as to be adapted to engage a rod received in the head and wherein the closure structure is adapted to operably urge the rod against the dome upon the closure structure being positioned in the head.

14. A polyaxial bone screw assembly for implantation in a human bone comprising:
a) an elongate shank having a body for fixation in a bone and a capture structure extending from the body, the capture structure having a top and a radially outer surface with a first helically wound guide and advancement structure; and
b) a head having a base and a top portion, the head top portion having an open channel, the base having a lower opening with a second helically wound guide and advancement structure therein that is sized and shaped to rotatingly mate with the first guide and advancement structure, the base further having a cavity openly joined to the opening, the channel communicating with the cavity, the cavity communicating with an exterior of the base through the opening, during assembly the capture structure being positionable in the cavity upon operable rotation of the first guide and advancement structure with the second guide and advancement structure until a disengagement between the first and second guide and advancement structures occurs such that the capture structure is substantially in the cavity and the shank body is exterior of the cavity whereby the shank capture structure can only be loaded into the head from below through the opening and thereafter locked in position relative to the head, the first and second guide and advancement structures configured for frictional engagement when the capture structure is urged toward the opening without rotation while the capture structure is within the head such that the shank body is locked in a fixed angular position with respect to the head.

15. The assembly of claim 14 wherein the first and second guide and advancement structures are first and second threads.

16. The assembly of claim 15 wherein the first thread is an inverted buttress thread.

17. The assembly of claim 14 wherein the capture structure has a lower substantially spherical surface, a portion of the spherical surface configured for frictional engagement with the second guide and advancement structure.

18. The assembly of claim 14 wherein the capture structure has a tool engagement formation disposed thereon adapted for non-slip engagement by a tool for driving the shank body into bone.

19. The assembly of claim 18 wherein the capture structure tool engagement formation is an axial projection having a hexagonal profile.

20. The assembly of claim 19 wherein the tool engagement formation is a projection and the capture structure has a tool seating surface, the projection and the tool seating surface partially defining a recess adapted for receiving a driving tool engaged with the tool engagement projection and wherein the driving tool is adapted to be in contact with the tool seating surface when driving the shank body into bone.

21. The assembly of claim 20 wherein the capture structure has at least one engagement wall disposed perpendicular to the tool seating surface and spaced from the projection, the engagement wall at least partially defining the recess for receiving the driving tool and wherein the driving tool is adapted to be in contact with the tool seating surface, the projection and the engagement wall when driving the shank body into bone.

22. The assembly of claim 14 wherein the shank is cannulated from the top to a bottom thereof.

23. The assembly of claim 14 further comprising a closure structure insertable into the head, the closure structure being adapted to operably urge the shank in a direction to frictionally lock the capture structure to the head, thereby locking the shank body in a selected angle with respect to the head.

24. The assembly of claim 23 wherein:
  (a) the head has upstanding spaced arms defining the open channel, the arms having a third guide and advancement structure on an inside surface thereof; and
  (b) the closure structure being sized and shaped to be positionable between the arms for closing the channel, the closure structure having a fourth guide and advancement structure for rotatably mating with the third guide and advancement structure.

25. The assembly of claim 24 wherein the capture structure top has a dome sized and shaped to extend into the channel so as to be adapted for engagement with a rod when received in the head and wherein the closure structure is adapted to operably urge the rod against the dome upon the closure structure being positioned in the head.

26. A polyaxial bone screw assembly for implantation into a human spine comprising:
  a) an elongate shank having a body for fixation to a bone and a capture structure extending from and integral with the body, the capture structure having a top, a radially outward facing surface with a first helically wound guide and advancement structure, and a tool engagement formation disposed adjacent the top, the tool engagement formation having a projection and a recessed tool seating surface having a bottom and an outer wall, both the bottom and outer wall sized and shaped for receiving and frictionally engaging a driving tool engaged with the tool engagement projection when driving the shank body into bone; and
  b) a head having a base with an inner surface defining a cavity, a portion of the inner surface having a second helically wound guide and advancement structure sized and shaped to rotatingly mate with the first guide and advancement structure, the base cavity communicating with an exterior of the base through an opening associated with the second guide and advancement structure such that the shank capture structure can only be upward loaded into the head through the lower opening in the head, the capture structure being pivotally disposed and captured in the cavity upon operable rotation of the first guide and advancement structure with the second guide and advancement structure until the first guide and advancement structure is disengaged from the second guide and advancement structure;
  (c) the head has upstanding spaced arms defining an open channel, the arms having a third guide and advancement structure on an inside surface thereof, the channel communicating with the cavity;
  (d) a closure structure insertable into an upper opening of the head, the closure structure being adapted for operably urging the shank in a direction to operably urge the shank capture structure against the head so as to frictionally lock the capture structure to the head, thereby locking the shank body in a selected angular position with respect to the head; and
  (e) the closure structure being sized and shaped to be positionable between the arms for closing the channel, the closure structure having a fourth guide and advancement structure for rotatably mating with the third guide and advancement structure.

27. The assembly of claim 26 wherein the capture structure top has a dome sized and shaped to extend into the channel when the capture structure is urged against the opening, the dome being adapted for engagement with a rod when received in the head and wherein the closure structure is adapted to operably urge the rod against the dome upon the closure structure being positioned in the head.

* * * * *